United States Patent [19]
Friedman

[11] Patent Number: 4,774,329
[45] Date of Patent: Sep. 27, 1988

[54] CONTROLLED RELEASE AGENT FOR CETYLPYRIDINIUM CHLORIDE

[75] Inventor: Robert B. Friedman, Chicago, Ill.

[73] Assignee: American Maize-Products Company, Stamford, Conn.

[21] Appl. No.: 81,644

[22] Filed: Aug. 4, 1987

[51] Int. Cl.$^4$ .................. C08B 37/16; A61K 31/00
[52] U.S. Cl. .................. 536/103; 536/106; 514/358; 514/964; 514/968; 424/409; 424/445; 424/447; 424/468; 424/488
[58] Field of Search ............. 424/409, 445, 447, 468, 424/488; 536/103, 106; 514/358, 964, 965

[56] References Cited

U.S. PATENT DOCUMENTS

| | | | |
|---|---|---|---|
| 3,420,789 | 1/1969 | Solms | 536/106 |
| 3,472,835 | 10/1969 | Buckler et al. | 536/46 |
| 4,274,985 | 1/1981 | Szejtli et al. | 525/54.2 |
| 4,357,468 | 11/1982 | Szejtli et al. | 536/56 |
| 4,472,373 | 9/1984 | Ryan | 424/54 |
| 4,576,950 | 3/1986 | Puritch | 514/358 |
| 4,727,064 | 2/1988 | Pitha | 514/965 |

OTHER PUBLICATIONS

Die Starke-Properties of Cyclodextrins-Part III-Cyclodextrin-Epichlorhydrin Resins: Preparation and Analysis-Wiedenhof et al.-pp.119-123.
Die Starke-Properties of Cyclodextrins-Part IV-Features and Use of Insoluble Cyclodextrin-Epichlorohydrin-Resins-Wiedenhof-pp. 163-166.
Die Starke-Properties of Cyclodextrins-Part V-Inclusion Isotherms and Kinetics of Inclusion of Benzoic Acid and m-Chlorobenzoic Acid on Beta-E25 Cyclodextrin-Epichlorohydrin Resin-Wiedenhof et al.-pp. 129-132.
Bull. Environm. Contam. Toxicol 25 (1980)-Adhesion-Binding of 2,2',4,4',5,5'-Hexachlorobiphenyl to Glass and Plastic: A Possible Source of Error for PCB Analysis-M. G. Pepe et al.-pp. 936-940.
Environm. Science & Technology-vol. 10, No. 4, Apr. 1976-Adsorption of Polychlorinated Biphenyls from Aqueous Solutions and Sewage-J. Lawrence et al.-pp. 381-383.
Bull. Environm. Contam. Toxicol. 24 (1980)-Flux of Aroclor 1254 Between Estuarine Sediments and Water-Wildish et al.-pp. 20-26.
Fisheries Research Board of Canada-Manuscript Report Series-No. 1083-Polychlorinated Biphenyls: Determination by Optical Methods, Solubility and Solubilization in Water, Preliminary Results of Toxicity to Salmon-Zito-Mar. 1970.

Primary Examiner—C. Warren Ivy
Assistant Examiner—Alex H. Walker
Attorney, Agent, or Firm—Lucas & Just

[57] ABSTRACT

A complex of cyclodextrin and cetylpyridinium chloride is disclosed as a controlled release agent of cetylpyridinium chloride. The cyclodextrin can be either cyclodextrin molecule, a polymer of cyclodextrin or modified cyclodextrin. The method of forming the complex is also disclosed.

11 Claims, 1 Drawing Sheet

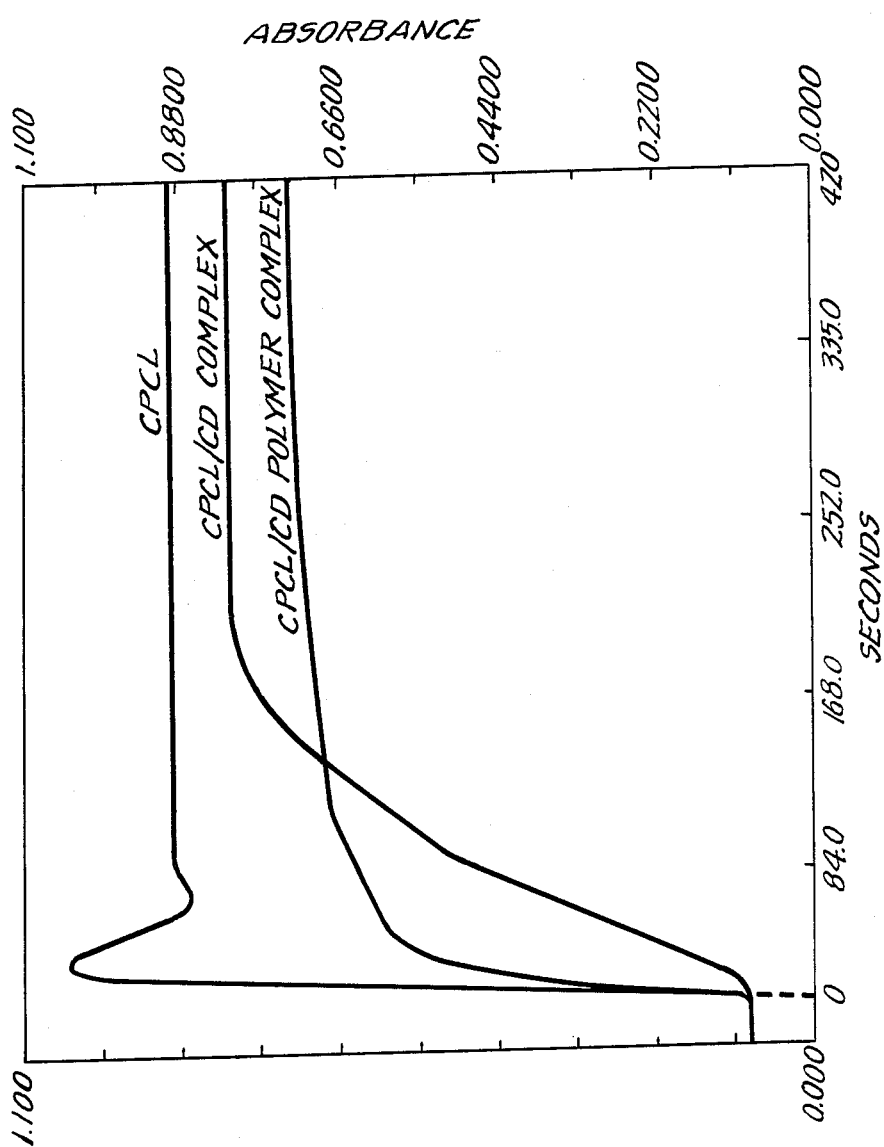

CONTROLLED RELEASE AGENT FOR CETYLPYRIDINIUM CHLORIDE

This invention relates to controlled release of cetylpyridinium chloride and more particularly to a complex formed between cyclodextrin and cetylpyridinium chloride and the use of the complex as a controlled release agent for cetylpyridinium chloride.

Cetylpyridinium chloride, also known as 1-hexadecylpyridinium chloride, is a well-known antimicrobial agent which is widely used as an antiseptic and disinfectant.

A major drawback to the use of cetylpyridinium chloride is its water solubility. Cetylpyridinium chloride is highly water soluble and rapidly dissolves in water. When applied to a wound, normal perspiration and contact with water by bathing or washing tends to remove the cetylpyridinium chloride from the treated area fairly rapidly. This requires frequent reapplication. It is highly desirable to have a means to control the release of cetylpyridinium chloride especially in aqueous environments such as human skin.

Applicants have now discovered that a complex of cetylpyridinium chloride and cyclodextrin acts as a controlled release agent for cetylpyridinium chloride. Such a complex provides a means for the controlled release of cetylpyridinium chloride to its surrounding environment. The controlled release agent of the present invention is formed with cetylpyridinium chloride and a cyclodextrin, a modified cyclodextrin or a cyclodextrin polymer.

The use of cyclodextrin polymers as a filter for various components is known. Cyclodextrin polymers are disclosed in U.S. Pat. Nos. 3,472,835; 4,274,985; and 4,357,468. The '835 patent teaches a cyclodextrin polymer as a filter from a vapor phase. The '985 patent discloses a cyclodextrin-polyvinyl alcohol polymer for use as a filter for nicotine (1-methyl-2-(3-pyridyl) pyrrolidine) from cigarette smoke and for benzene in water. The '468 patent uses a cyclodextrin-cellulose polymer for use as a filter for benzene, phenol, cresol in aqueous solutions, and tar and nicotine from cigarette smoke. These patents relate to removing simple, single aromatic compounds.

This was truly surprising that a complex of cetylpyridinium chloride and cyclodextrin acts as an agent for the controlled release of cetylpyridinium chloride because cetylpyridinium chloride is so highly soluble in water. It was also unexpected that cetylpyridinium chloride forms a complex in a cyclodextrin. Cetylpyridinium chloride contains both an aromatic portion (pyridinium portion) and an aliphatic portion (cetyl chain) which makes the formation of a complex between the cetylpyridinium chloride and cyclodextrin unexpected.

FIG. 1 illustrates the controlled release of cetylpyridinium chloride using the complex of the present invention.

The use of the complex of the present invention permits a lower initial dosage of cetylpyridinium chloride and a decrease in need for repeated treatments of cetylpyridinium chloride in order to maintain a level of antimicrobial activity.

Cyclodextrins also called "Schardinger Dextrins" are cyclic oligosaccharides composed of glucose units bonded together by alpha 1,4 bonds. The six membered ring structure is called alpha-cyclodextrin, the seven membered ring is beta-cyclodextrin and the eight membered ring is gamma-cyclodextrin. The cyclodextrins have different chemical and physical properties from the linear ologosaccharides derived from starch in that they are non-reducing dextrins.

As is also well-known, cyclodextrins are produced from starch of any selected plant variety such as corn, potato, waxy maize and the like which may be modified or unmodified starch derived from cereal or tuber origin and the amylose or amylopectin fractions thereof. The selected starch in aqueous slurry at selected concentration up to about 35% by weight solids is usually liquefied as by gelatinization or treatment with a liquefying enzyme such as bacterial alpha-amylase enzyme and then subject to treatment with a cyclodextrin glucosyl transferases enzyme (CGT) to form the cyclodextrins.

The amount of the individual alpha, beta and gamma-cyclodextrins produced by treating the starch with the CGT enzyme will vary depending on the selected starch, selected CGT enzyme and processing conditions. The parameters to select for the CGT enzyme conversion for the desired result in the amount of each individual cyclodextrin to be produced is conventional and well-described in the literature.

Conventionally, the DE of the liquefied starch is maintained below about 20 DE, the starch solids concentration is below about 35% by weight, the pH for conversion may be about 4.5 to 8.5 at a selected temperature from ambient and up to about 75° C. for a selected period of time typically from about 10 hours up to seven days and more. The amount of CGT enzyme used for conversion is conventional and well-known in the art.

Separation and purification of the cyclodextrin thus obtained is conventional and well-known to those of skill in the art.

The preferred cyclodextrin for use in the present invention is beta-cyclodextrin because of its relative availability and relative low cost, but any cyclodextrin or mixture of cyclodextrins can be used to form the polymer.

Formation of the cyclodextrin polymer is carried out in a conventional manner. Suitable means include reacting the cyclodextrin with a cross-linking agent to form a cyclodextrin polymer. A suitable means for performing such a reaction to form beads of the cyclodextrin polymer is disclosed in an article written by Wiedenhof et al. in Vol. 21 at page 119 of Die Starke 1969. Typically, a dry cyclodextrin is wetted with water and then dissolved in a basic solution, typically 30% sodium hydroxide. To this is added sodium borohydride to prevent the cyclodextrin from oxidizing. This aqueous solution is added to a solvent such as methyl isobutyl ketone containing a surfactant such as polyethoxylated octyl phenyl ether. The mixture is then stirred to form an emulsion of cyclodextrin solution in the solvent. The cyclodextrin is the disperse phase and generally in small particle-like cells. To this emulsion, a cross-linking agent is added in an amount sufficient to allow the cyclodextrin to form a cross-linked outer surface and preferably enough to allow the cyclodextrin to become a cross-linked bead. Typically, about 34% molar excess of cross-linking agent is added based on the moles of cyclodextrin in the emulsion i.e. 34 moles of cross-linking agent per one mole of cyclodextrin. In this manner water-insoluble beads of cross-linked cyclodextrins are formed. Suitable cross-linking agents include epichlorohydrin, trimetaphosphate, phosphorous oxychloride and butanediol diglycidyl ether. Preferably etherifying cross-linking agents are used such as epihalohydrins like epichlorohydrin and epibromohydrin or di epoxide compounds. The size of the beads can be adjusted to any conventional size depending on the final use of the controlled release agent of the present invention.

Other conventional means of forming a polymer with cyclodextrins are possible, however, commercially for such purpose the formation of water-insoluble beads as described above is preferred.

Another method of forming a cyclodextrin polymer is to use already formed polymers as a backbone and onto that backbone attach cyclodextrins. The backbone and attached cyclodextrins may be insoluble in water just as the cross-linked beads of cyclodextrins are. Suitable backbones are polyurethane, cellulose, polyvinyl alcohol and polystyrene derivatives. In such instances, the cyclodextrin is preferably covalently bonded to the backbone. The method for forming a cyclodextrin polymer on a backbone of another, already formed polymer is conventional and accomplished in a conventional manner.

Formation of modified cyclodextrin is carried out in a conventional manner. The only requirement is that the cavity of the cyclodextrin does not become too restricted or capped to prevent use of the modified cyclodextrin as a controlled release agent with cetylpyridinium chloride. Modified cyclodextrin includes hydroxypropyl and hydroxyethyl cyclodextrins.

In order to form a complex between cetylpyridinium chloride and a cyclodextrin whether the cyclodextrin is in the form of a cyclodextrin molecule, a modified cyclodextrin or a cyclodextrin polymer, a mixture of cyclodextrin molecules and cetylpyridinium chloride is formed in water and stirring for a period of time sufficient to form the complex. The complex is then removed from the water and dried. The dried complex is then ready for use.

The amount of cetylpyridinium chloride to cyclodextrin molecule in the solution is about ½:1 to about 4:1 molar ratio of cetylpyridinium chloride:cyclodextrin molecules and more preferably about 1½:1 ratio of cetylpyridinium chloride:moles cyclodextrin molecules. The term cyclodextrin molecules is used because the formation of the complex between cyclodextrin and cetylpyridinium chloride depends on the number of available cavities. There are more cavities available in a mole of cyclodextrin polymer than in a mole of cyclodextrin.

The addition of the cetylpyridinium chloride to the mixture can be either in solid form or in an aqueous solution. Preferably, when the cetylpyridinium chloride is added to a solution of modified cyclodextrin or cyclodextrin, it is added as an aqueous solution, while when it is added to a polymer of cyclodextrin, it is added as a solid.

The mixing of the cyclodextrin and cetylpyridinium chloride is conducted in a conventional manner using conventional equipment. In forming the mixture with cyclodextrin molecules, it has been found that preferably the temperature of the mixture is elevated above room temperature and preferably the temperature of the cyclodextrin and cetylpyridinium chloride mixture is maintained at bout 85° C. To remove the complex from the mixture then the mixture is cooled and the complex precipitates out of solution. The mixing of the polymer and cetylpyridinium chloride is preferably carried out at room temperature.

The pH of the mixture is between about 3 to about 12 and preferably about neutral. The pH can be adjusted in a conventional manner.

The period of time sufficient to form a complex between a cyclodextrin and cetylpyridinium chloride varies with the form of the cyclodextrin. It has been found that when cyclodextrin molecules are used, about 3 to about 5 hours of mixing between the cyclodextrin and the cetylpyridinium chloride at a temperature of about 85° C. produces good results. With a polymer of cyclodextrin, good results have been obtained after about 12 to about 16 hours of mixing at room temperature.

In forming a solution of cyclodextrin molecules with cetylpyridinium chloride, good results have been obtained when a slurry of cyclodextrin molecules is formed at about 35% solids.

Recovery of the complex formed between the cyclodextrin molecules and cetylpyridinium chloride is accomplished preferably by allowing the solution to cool to room temperature which causes the complex to precipitate out of solution. Removal of the precipitate is done in a conventional manner.

Recovery of the complex formed between the cyclodextrin polymer and cetylpyridinium chloride is accomplished by filtering the polymer which is typically insoluble from the solution in a conventional manner.

Drying the recovered complex is done in a conventional manner. Good results have been obtained by air drying the complex.

Use of the complex is accomplished by incorporating the complex in a lotion or salve for treatment of a wound or other area. It is also possible to incorporate the complex in a bandage such that the cetylpyridinium chloride is released to the effected area in a controlled manner. Incorporation of the complex into a bandage allows for the slow release of cetylpyridinium chloride to the damaged area.

Further details of the present invention will be understood by reference to the following examples which illustrate several embodiments of the present invention.

EXAMPLE 1

This example illustrates the making of a polymer of cyclodextrin.

A dry beta-cyclodextrin which was made in a conventional manner, was cross-linked with epichlorohydrin to form beads of water-insoluble cyclodextrin polymer. In order to form the beads, 100 grams of dry beta-cyclodextrin was wetted by adding 100 ml of water to the cyclodextrin. The wetted cyclodextrin was then added to 160 grams of 30% NaOH. To this was added a small amount, 200 milligrams, of sodium borohydride to prevent the cyclodextrin from oxidizing. This mixture was added to 3.5 liters of methyl isobutyl ketone as a reaction medium along with 20 mls of polyethoxylated octyl phenyl ether, a well-known surfactant. The mixture was then stirred and an emulsion formed. The cyclodextrins were in the disperse phase of the emulsion. This mixture was then equilibrated by stirring vigorously for five minutes.

After equilibration, the emulsion, a molar ratio of 34 parts of epichlorohydrin per one part of cyclodextrin, was added and the cyclodextrin was cross-linked to form a water-insoluble cyclodextrin-containing polymer bead. The beads were recovered by filtering the reaction mass.

EXAMPLE 2

This example illustrates the formation of a complex between beta cyclodextrin and cetylpyridinium chloride.

To a vessel containing 55 ml of water, 57.26 grams of a beta cyclodextrin was added. The temperature in the vessel was maintained at around 85° C. and 15.55 grams of an aqueous solution of cetylpyridinium chloride monohydrate was added dropwise to the solution of cyclodextrin and water. The solution of cetylpyridinium chloride monohydrate was prepared by adding 15.5 grams of solid cetylpyridinium chloride monohydrate to 50 ml of water. The pH of the solution was maintained around 7. After about 3 to 4 hours, the solution was allowed to cool to room temperature so that a precipitate formed. The precipitate was collected on filter paper and air dried.

In this manner a complex was formed in accordance with the present invention.

EXAMPLE 3

This example illustrates making a complex with a polymer of beta cyclodextrin and cetylpyridinium chloride.

In a vessel containing 25.16 grams of deionized water, 50.55 grams of a polymer of cyclodextrin in the form of insoluble beads was added to form a slurry. To this slurry was added 15.97 grams of solid cetylpyridinium chloride monohydrate and the mixture was stirred for five days. Throughout the mixing step the temperature was room temperature, about 20° C. The pH was neutral. The polymer was transferred to a scintered glass funnel and dried in the funnel.

It will be appreciated that the cyclodextrin polymer was insoluble in water and that when stirring was discontinued the beads fell under gravity to the bottom of the container.

In this manner a complex was formed in accordance with the present invention.

EXAMPLE 4

To illustrate the control release aspect of the present invention, a Beckman Spectrophotometer was modified to contain a flow through cell in accordance with direction from the Beckman Company. This allowed for continuous readings of light absorbence to determine the amount of cetylpyridinium chloride in an aqueous solution containing the complex of the present invention.

The complex formed in Examples 2 and 3 were tested against the mere addition of cetylpyridinium chloride as a solid to water to determine the rate at which cetylpyridinium chloride goes into solution. Cetylpyridinium chloride has a distinct U.V. absorbence spectrum. FIG. 1 illustrates the various rates at which cetylpyridinium chloride dissolved in solution. Time is the horizontal axis and absorbence measured by the spectrophotometer is the vertical axis. From the zero point in time it can be seen that in about 90 seconds the solid cetylpyridinium chloride was completely dissolved. With respect to the complex of Example 2, after about 230 seconds all the cetylpyridinium chloride was dissolved from the complex. This is a decrease of about 2½ times the rate at which non-complexed cyclodextrin dissolves. With respect to the complex of cetylpyridinium chloride and cyclodextrin polymer, Example 3, even after 420 seconds, not all of the cetylpyridinium chloride had dissolved. This shows a decrease of over five times the rate at which cetylpyridinium chloride dissolves.

The steep rise of absorbence in the first few minutes with respect to the complex of the present invention are thought to be due to the presence of cetylpyridinium chloride on the surface of the complex. This provides an advantage in that there is an initial high dose of cetylpyridinium chloride to the wound area and then after this initial dose, a slow and continuous treatment of the wound.

Cetylpyridinium bromide could also be used to form a complex with cyclodextrin.

It will be understood that it is intended to cover all changes and modifications of the preferred embodiments herein chosen for the purpose of illustration which do not constitute a departure from the spirit and scope of the invention.

What is claimed is:

1. A controlled release agent for cetylpyridinium chloride comprising a complex formed between cyclodextrin and cetylpyridinium chloride.

2. The controlled release agent of claim 1 wherein the cyclodextrin is a beta cyclodextrin.

3. The controlled release agent of claim 1 wherein the cyclodextrin is produced by reaction of cyclodextrin with a crosslinking agent or by reaction of cyclodextrin with a previously formed polymer backbone.

4. The controlled release agent of claim 1 wherein the cyclodextrin has been modified in a manner such that the cavity of the cyclodextrin is not too restricted or capped to prevent complex formation with said cetylpyridinium chloride.

5. A method for making a controlled release agent for cetylpyridinium chloride comprising the steps of:
    (a) mixing cyclodextrin and cetylpyridinium chloride together in water for a sufficient period of time to form a complex;
    (b) recovering said complex from water; and
    (c) drying said recovered complex.

6. The method of claim 5 wherein the cyclodextrin is a beta cyclodextrin.

7. The method of claim 5 wherein the cyclodextrin is produced by reaction of cyclodextrin with a cross-linking agent or by reaction of cyclodextrin with a previously formed polymer backbone.

8. The method of claim 5 wherein the cyclodextrin has been modified in a manner such that the cavity of the cyclodextrin is not too restricted or capped to prevent complex formation with said cetylpyridinium chloride.

9. The method of claim 5 wherein the temperature is about 85° C. during the mixing step and the period of time sufficient to form the complex is about 12 hours.

10. The method of claim 7 wherein the temperature during the mixing step is about room temperature and the period of time sufficient to form the complex is about 3 hours.

11. The method of claim 5 wherein the amount of cetylpyridinium chloride and cyclodextrin is in a ratio of about 0.5:1 to about 4:1 of moles of cetylpyridinium chloride:moles of cyclodextrin molecule.

\* \* \* \* \*

UNITED STATES PATENT AND TRADEMARK OFFICE
CERTIFICATE OF CORRECTION

PATENT NO. : 4,774,329

DATED : September 27, 1988

INVENTOR(S) : Robert B. Friedman

It is certified that error appears in the above-identified patent and that said Letters Patent are hereby corrected as shown below:

Column 6, line 54, cancel beginning with "9. The method of" to and including "about 3 hours." in column 6, line 60, and insert the following claims:

9. The method of claim 6 wherein the temperature is about 85°C during the mixing step and the period of time sufficient to form the complex is between about 3 to about 5 hours.

10. The method of claim 7 wherein the temperature during the mixing step is about room temperature and the period of time sufficient to form the complex is between about 12 to about 16 hours.

Signed and Sealed this

Twenty-eighth Day of February, 1989

Attest:

DONALD J. QUIGG

Attesting Officer     Commissioner of Patents and Trademarks